United States Patent [19]

Thomas

[11] Patent Number: 5,184,044
[45] Date of Patent: Feb. 2, 1993

[54] DENTAL CURING LAMP

[75] Inventor: Brian J. Thomas, Phoenix, N.Y.

[73] Assignee: Welch Allyn, Inc., Skaneateles Falls, N.Y.

[21] Appl. No.: 565,732

[22] Filed: Aug. 13, 1990

[51] Int. Cl.$^5$ .............................................. H01J 61/20
[52] U.S. Cl. .................................... 313/638; 313/639; 313/642
[58] Field of Search ............... 313/638, 639, 642, 620, 313/623

[56] References Cited

U.S. PATENT DOCUMENTS

| | | | |
|---|---|---|---|
| 3,234,421 | 2/1966 | Reiling | 313/25 |
| 3,259,777 | 7/1966 | Fridrich | 313/638 |
| 3,379,916 | 4/1968 | Delrieu et al. | 313/642 |
| 3,577,029 | 5/1971 | Koury et al. | 313/638 |
| 3,868,513 | 2/1975 | Gonser | 250/504 |
| 4,112,335 | 9/1978 | Gonser | 315/241 R |
| 4,161,672 | 7/1979 | Cap et al. | 313/620 |
| 4,202,999 | 5/1980 | Holle et al. | 313/317 |
| 4,221,994 | 9/1980 | Friedman et al. | 315/224 |
| 4,229,658 | 10/1980 | Gonser | 250/504 H |
| 4,298,806 | 11/1981 | Herold | 250/504 H |
| 4,309,617 | 1/1982 | Long | 250/504 H |
| 4,385,344 | 5/1983 | Gonser | 362/32 |
| 4,412,134 | 10/1983 | Herold et al. | 250/504 R |
| 4,445,858 | 5/1984 | Johnson | 433/131 |
| 4,450,139 | 5/1984 | Bussiere et al. | 422/186.3 |
| 4,491,453 | 1/1985 | Koblitz et al. | 433/217 |
| 4,504,231 | 3/1985 | Koblitz et al. | 433/228 |
| 4,514,174 | 4/1985 | Dougherty et al. | 433/226 |
| 4,515,195 | 5/1985 | Gonser | 362/281 |
| 4,528,478 | 7/1985 | Rothwell, Jr. et al. | 313/631 |
| 4,538,070 | 8/1985 | Herold et al. | 250/504 R |
| 4,546,261 | 10/1985 | Gonser et al. | 250/492.1 |
| 4,582,998 | 4/1986 | Gonser et al. | 250/492.1 |
| 4,594,529 | 6/1986 | De Vrijer | 313/620 |
| 4,608,622 | 8/1986 | Gonser | 362/32 |
| 4,615,679 | 10/1986 | Wyatt | 433/229 |
| 4,623,795 | 11/1986 | Knopp et al. | 250/504 H |
| 4,716,296 | 12/1987 | Bussiere et al. | 250/504 H |
| 4,795,943 | 1/1989 | Antonis et al. | 313/620 |
| 4,992,700 | 2/1991 | Lake | 313/639 |

FOREIGN PATENT DOCUMENTS

| | | | |
|---|---|---|---|
| 35347 | 10/1971 | Japan | 313/642 |
| 53172 | 5/1978 | Japan | 313/642 |
| 1-137555 | 5/1989 | Japan | 313/639 |

Primary Examiner—Donald J. Yusko
Assistant Examiner—Michael Horabik
Attorney, Agent, or Firm—Wall and Roehrig

[57] ABSTRACT

A low watt metal halide discharge lamp for use in photo-curing photo-curable compositions. The lamp comprises an envelope made of light transmissive material having walls that define an arc chamber volume. Contained within the arc chamber volume is a fill of mercury, inert gas and a metal halide additive that includes indium iodide or indium triiodide. The mercury and metal halide are adapted to substantially vaporize during operation of the lamp and produce radiant energy substantially within the wavelength range between about 400 and 500 nm. Extending into the arc chamber volume is a pair of electrodes having electrode tips spaced apart from one another by a predetermined distance. The lamp also includes a pair of inlead assemblies electrically coupled to a pair of electrodes respectively. The inlead assemblies pass from the electrodes through a sealed section to the exterior of the lamp.

16 Claims, 4 Drawing Sheets

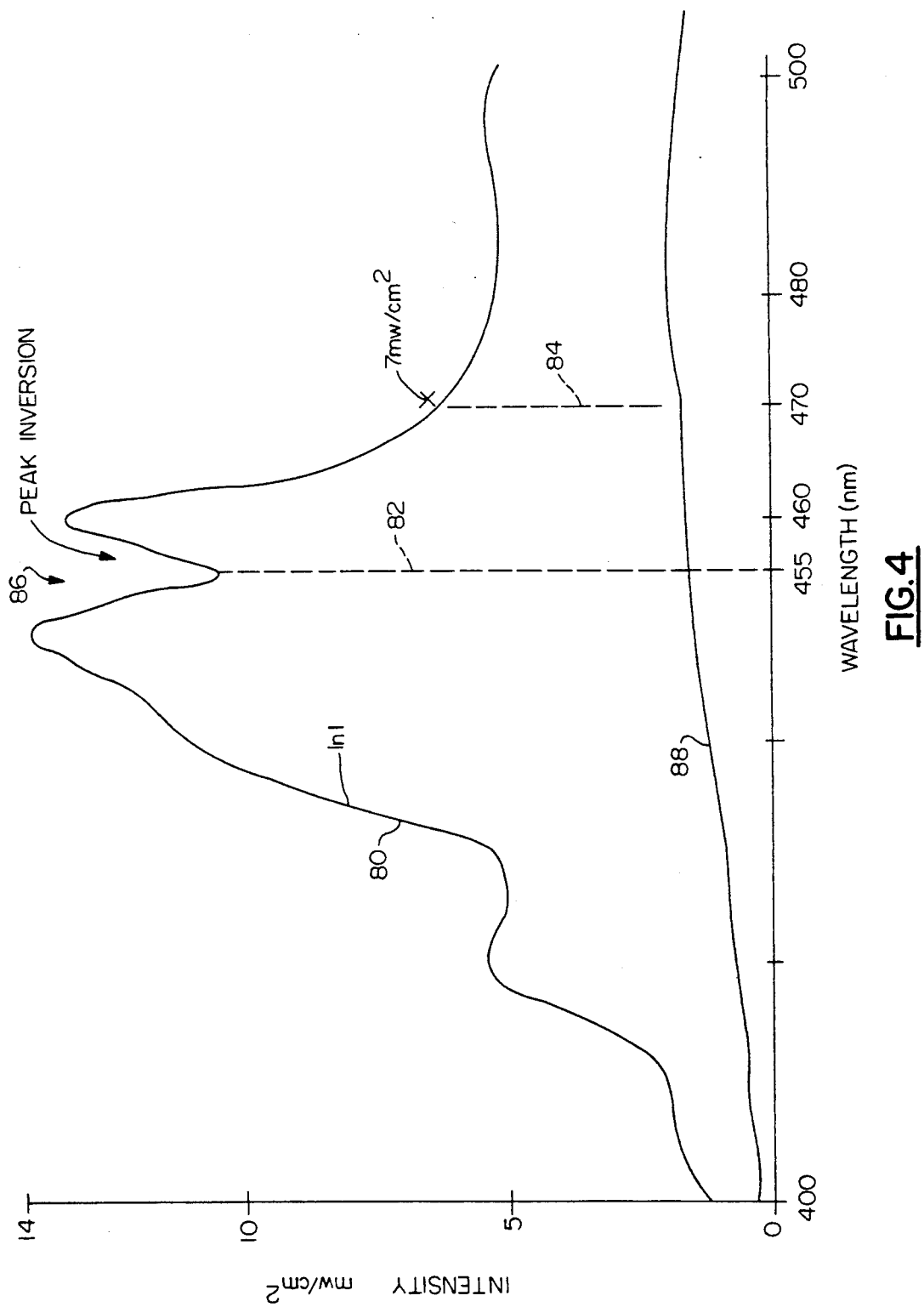

DENTAL CURING LAMP

BACKGROUND OF THE INVENTION

This invention relates in general to apparatus for providing radiant energy in a relatively narrow wavelength band for the purpose of photo-curing materials such as photo-curable dental restoration material or compositions. The invention is more specifically directed to a low-power high-intensity curing lamp to be used in dental curing apparatus.

In the field of dentistry, there is a growing use of dental compositions, e.g., sealants, dental filling and restoration materials, dental impression materials, and other compounds, that rely on photoinitiators to react in the presence of light. Some of these materials cure, or harden, upon exposure to blueviolet light, specifically light between 400 and 500 nanometers in wavelength. The photoinitiators have a peak sensitivity in the vicinity of about 470 nm.

In order to treat a patient, the dentist can prepare the material under subdued light, or in the presence of red light, whose longer wavelengths do not bring about curing of the material to the patient's tooth or teeth, e.g. by filling a cavity. Under these conditions, the material remains workable, then the dentist applies intense blueviolet light for a period of time to cure the material to a hardened state.

A number of photo-curable dental materials are known and available, and several typical compositions are described in U.S. Pat. Nos. 4,504,231; 4,514,174; and 4,491,453.

In order to cure the material, the dentist may apply the intense blueviolet light using a hand-held light gun. These guns typically have an electric lamp device within a housing, and an elongated light conduit to carry the light to the material within the patient's mouth. The material typically can require 60 to 90 seconds of curing time, and during this time the tip of the light conduit is in close contact with the patient's mouth. It is quite important that the distal tip of the conduit remain cool, and that there not be great amounts of infrared which can disrupt the curing process and possibly heat the patient's teeth causing discomfort or damage.

Also, for reasons of operator safety, the lamp or gun must keep stray radiation within safe limits, and produce neither ionizing ultraviolet radiation nor infrared radiation in significant amounts.

In order to produce light of sufficient intensity within a bandwidth for effective curing, the currently available devices require a rather powerful lamp that also generates significant radiation outside the optimal 400-500 nm range. Typically, a heat filter is required in the optical path of the light emitted from the lamp to block or absorb long-wavelength radiation. Heat management is a problem for these devices, and provisions must be included to keep the lamp and its surroundings from overheating.

Previous dental curing apparatus for this general purpose are described in U.S. Pat. Nos. 4,229,658; 4,385,344; and 4,546,261.

So a need exists in the dental curing art to devise a lamp that can operate at low enough power inputs so that excessive heat is not generated and, yet, generate high enough light intensity in an optimum wavelength range for effective photo-curing of dental compositions. Or, equivalently, a lamp is required with a relatively high spectral efficiency for an optimum wavelength range specified.

In the lamp arts, it has been known that metal halide discharge lamps have provided improved efficiencies compared to incandescent and other types of lamps. In a typical metal halide lamp, an envelope of vitreous silica material defines an arc chamber which contains a fill of mercury, inert gas, and a metal halide additive. Sealed in the arc chamber is a pair of refractory tungsten electrodes having tips spaced apart from one another. After an arc discharge is established between the electrode tips, the temperature of the arc chamber rapidly increases, causing the mercury and metal halide additives to vaporize. The mercury atoms and metal atoms of the metal halide are ionized and excited, causing emissions of radiation at spectrums characteristic of the respective metals. This radiation is substantially combined within the arc chamber to produce a resultant light output having an established intensity and spectral characteristic.

A disadvantage experienced with metal halide lamps is that at low power input levels (i.e., 35 watts and below), improved efficiencies have not been generally attainable. In addition, at such low power input levels, the spectral characteristics of the light emitted from such low watt lamps have not been adequately controllable.

In a copending application, now U.S. Pat. No. 5,144,201 Feb. 23, 1990 by Timothy W. Graham and Daniel C. Briggs, entitled Low Watt Metal Halide Lamp, assigned to the same assignee as this application, useful and efficient low watt metal halide discharge lamps are disclosed. These lamps achieve, at input powers of 35 watts and below, efficiencies and spectral control that are suitable for the above-described dental curing applications. However, a set of parameters for these low watt metal halide lamps had to be developed and a halide additive or combination of additives needed to be found in order to produce a high intensity lamp output within the desired wavelength range for dental curing applications.

OBJECTS AND SUMMARY OF THE INVENTION

It is an object of this invention to provide a dental curing lamp and apparatus which avoids the drawbacks of the prior art.

It is a more specific object of the invention to provide a new low watt metal halide discharge lamp suitable for photocuring organic monomer compositions such as photo-curable dental materials.

Another object of the present invention is to provide a low watt metal halide discharge lamp that emits its primary radiant energy output in the wavelength range of 400 to 500 nm to achieve relatively short photo-curing times of organic monomer compositions.

A further object of the present invention is to provide a low watt metal halide discharge lamp that emits its primary radiant energy output in the wavelength range of 400 nm to 500 nm to achieve relatively short photo-curing times of organic monomer compounds.

Still another object of the present invention is to provide a device for curing photo-curable dental compositions, which operates at low power and high efficiency.

It is another object of this invention to provide a dental material curing device that is simple and lightweight, and which remains cool in operation.

It is a further object of this invention to provide a dental material curing device which produces light predominantly in the 400–500 nm wavelength range, and which produces insignificant amounts of ultraviolet or infrared radiation.

These and other objects are attained in accordance with the present invention wherein there is provided a low watt metal halide discharge lamp for use in photocuring photo-curable compositions. The lamp, according to the present invention, comprises an envelope made of light transmissive material having walls that define an arc chamber volume. Contained within the arc chamber volume is a fill of mercury, inert gas and a metal halide additive that includes indium iodide or indium triiodide. The mercury and metal halide are adapted to substantially vaporize during operation of the lamp and produce radiant energy substantially within the wavelength range between about 400 and 500 nm. Extending into the arc chamber volume is a pair of electrodes having electrode tips spaced apart from one another by a predetermined distance. The lamp also includes a pair of inlead assemblies electrically coupled to the pair of electrodes respectively. The inlead assemblies pass from the electrodes through a sealed section to the exterior of the lamp.

In accordance with another aspect of this invention, a dental curing apparatus is provided for photo-curing photocurable material. The apparatus has a housing and a light source in the housing that produces substantially visible radiation that is concentrated predominantly in the wavelength range of about 400 nm to 500 nm. A light conduit rod, such as a fused fiber optic bundle or a liquid light pipe, carries the visible radiation out from the housing to a location of a quantity of the photo-curable material that is to be cured.

The light source comprises a low-power metal halide lamp that contains as its principal metal halide additive a halide salt of indium, such as InI or $InI_3$.

The lamp contains a sufficient quantity of the indium halide salt so that it has a high operating vapor pressure characterized by a spectral broadening of the discharge emission around the principal spectral line of indium, i.e. 455 nm, and a spectral line reversal or peak inversion at the position of that spectral line.

A hand-held dental curing lamp device of the invention includes the lamp positioned in the housing at one focus of an ellipsoidal reflector, so that the light from the lamp is concentrated at another focus at which the proximal end of the light conduit is positioned. The reflector can have a dichroic coating to reflect light in the range of 400 to 500 nm and pass the remaining wavelengths through the reflector. The device can have a shutter mechanism between the reflector and the distal end of the conduit to allow the dentist or other operator to control the beam of light without need to switch the quartz metal halide lamp on and off, and thus avoid waiting for lamp warm-up.

With this device, very little heat is produced, so heat management is simplified. The device operates with a low power metal halide lamp of the present invention, and produces sufficient light to cure typical photo-curable dental material rapidly, i.e., from several seconds to one or two minutes, depending on the material.

The above and many other objects, features, and advantages of this invention will be more fully appreciated from the ensuing description of a preferred embodiment, to be read in connection with the accompanying Drawing.

BRIEF DESCRIPTION OF THE DRAWING

FIG. 4 is a spectral chart showing the light emission characteristics of the lamp of FIG. 3.

DETAILED DESCRIPTION OF THE PREFERRED EMBODIMENT

Figure 1:
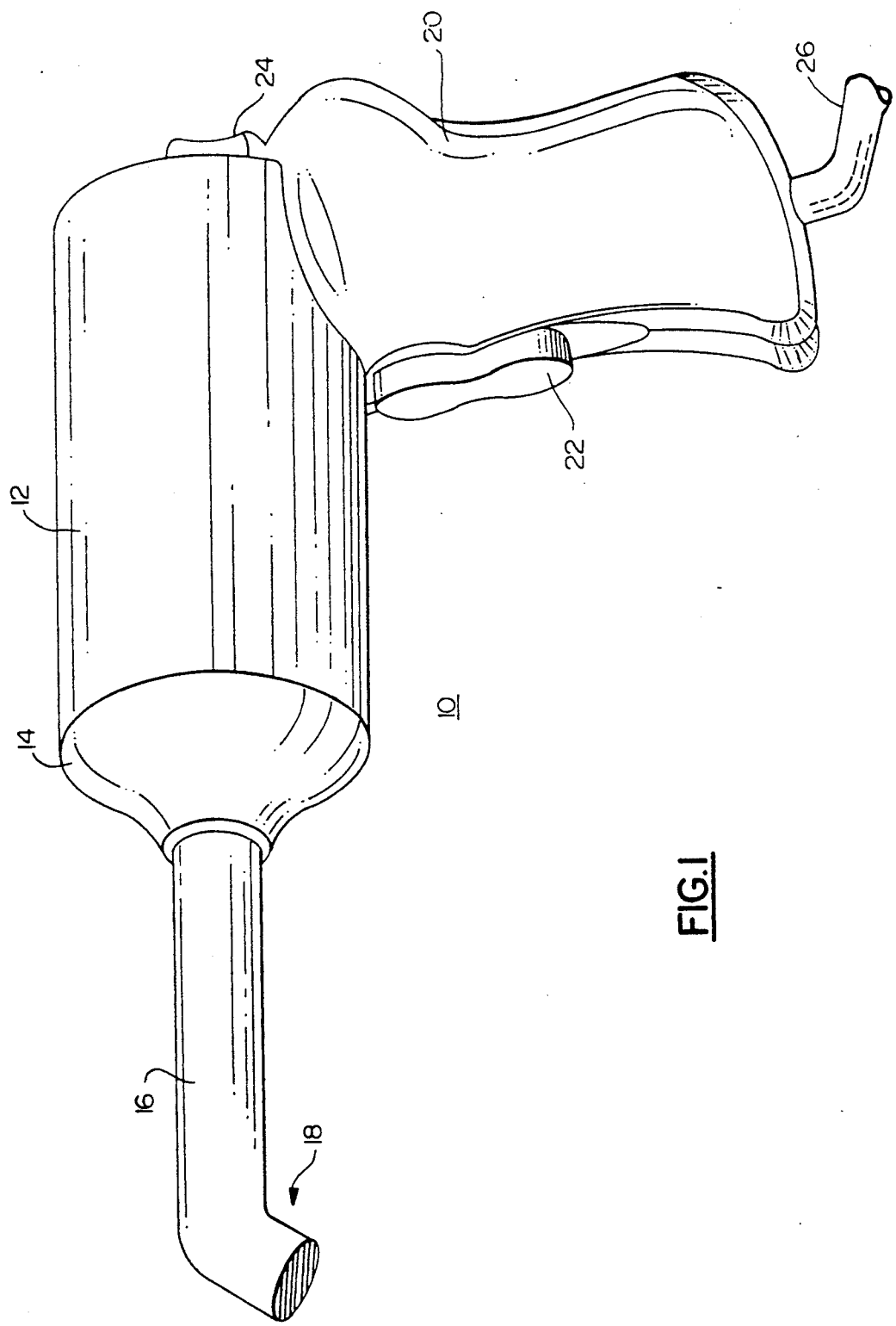
FIG. 1 is a perspective view of a dental light gun device according to an embodiment of this invention for curing dental compositions such as photo-curable restoration material or photocurable dental impression material.

With reference to the Drawing, and initially to FIG. 1 thereof, a dental irradiation unit 10, in the form of a light gun, has a generally tubular barrel or housing 12 with a cap 14 at the forward or distal side, and a light-conducting rod 16 that protrudes out from the cap. In this embodiment, the rod 16 is rigid, but has a bent tip 18 for access to rear surfaces of a patient's teeth. The unit 10 has a handle 20 at its rear or proximal side, with a trigger 22 for actuating a shutter mechanism within the housing 12. An on/off switch 24 is positioned for thumb actuation, and a power cord 26 extends from the lower end of the handle 20.

Figure 2:
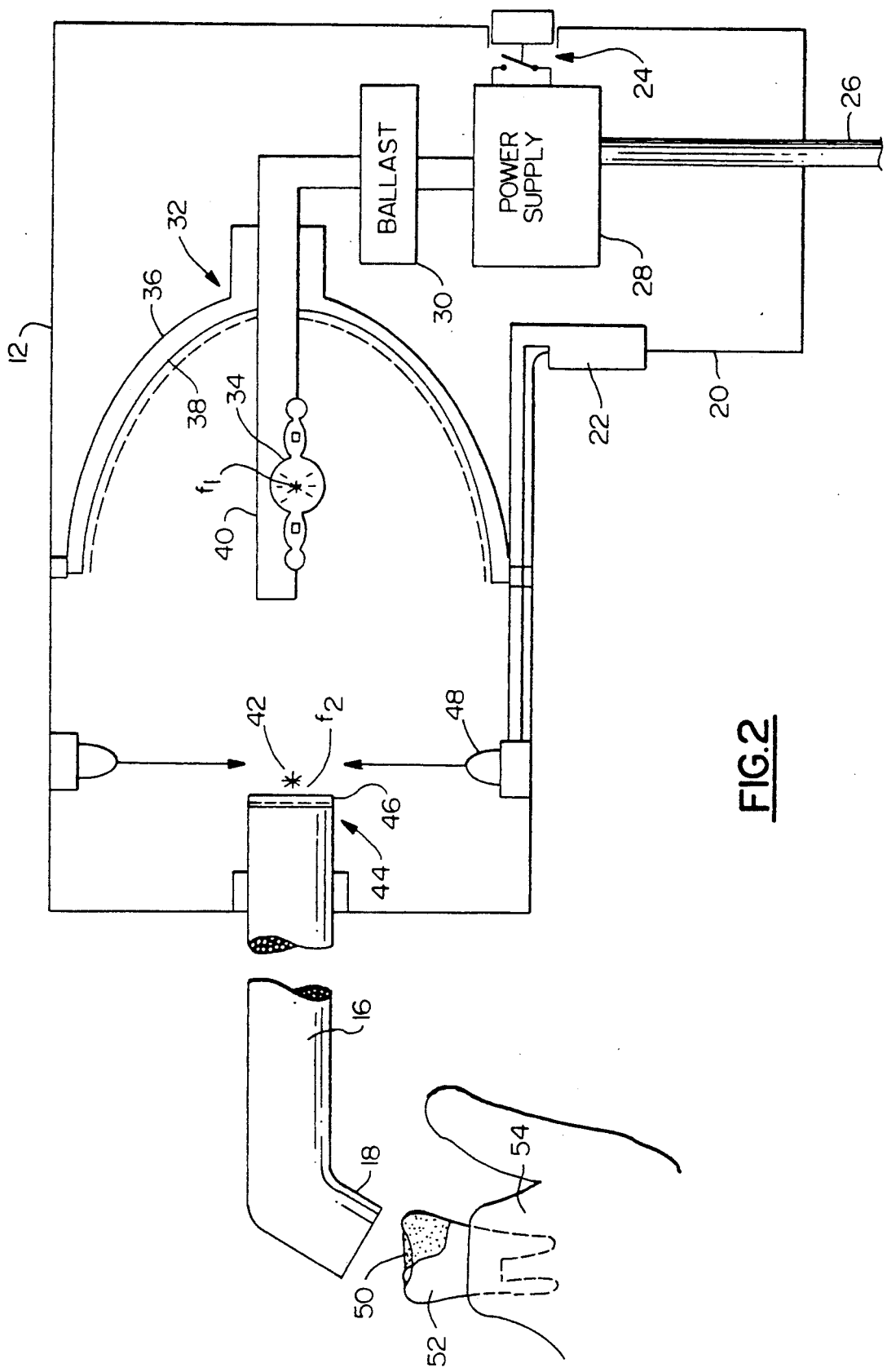
FIG. 2 is a schematic view of the device of this embodiment.

The internal construction of the unit 10 is shown generally in FIG. 2. The power cord 26 furnishes AC power to a power supply unit 28, which can be favorably positioned in the handle 20. The power supply unit 28 provides regulated DC power through a ballast circuit 30 to a lamp assembly 32 positioned in the barrel or housing 12 of the unit 10. The lamp assembly 32 has a low watt metal halide lamp 34, which is described in greater detail below with reference to FIG. 3. Lamp 34 is of low power (e.g., up to 35 watts, and preferably between 18 and 22 watts, here 20 watts) and produces a high radiant flux density and spectral efficiency in the wavelength range of 400 to 500 nm. The lamp 34 is positioned within an ellipsoidal reflector 36 that is provided with a dichroic reflective coating 38. The dichroic coating reflects wavelengths between 400 and 500 nm, but passes those wavelengths below 400 nm or above 500 nm. The lamp 34 is positioned at or adjacent a first focus 40 of the reflector 36, so that its light is reflected to concentrate at a second, conjugate focus 42 of the reflector. As shown in FIG. 2, a proximal end 44 of the light rod 16 is positioned within the housing 12 at or adjacent the conjugate focus 42 so that most of the light from the lamp 34 is directed to enter the light rod 16. As also shown, an infrared filter 46 is positioned at the end 44 of the rod 16 to exclude light having wavelengths in the range of 500–780 nm and residual infrared radiation.

A shutter 48, which is actuated by the trigger 22, is positioned between the lamp assembly 32 and the filter 46. The shutter can be one of a number of well-known designs.

As shown schematically, the light rod 16 directs the 400–500 nm visible radiation onto a quantity of dental filing or restoration material 50 within a tooth 52 in a patient's jaw 54. After the switch 24 has been switched on for a period sufficient for the lamp 34 to warm up to its stable operating condition, the dentist or dental technician can simply actuate the trigger 22 to open the shutter 48 and direct the light that emanates from the light rod 16 onto the dental material 50. This material cures to complete hardness in about six seconds to less than two minutes.

There are a large number of dental compositions available both for fillings and restorations, and also for molding dental impressions, and these are described, e.g., in U.S. Pat. Nos. 4,504,231, 4,514,174, and 4,491,453. These materials remain workable in subdued light or light of longer wavelengths, i.e. red light. The materials contain photoinitiators that are sensitive to wavelengths between 400 and 500 nm which, if present in significant strength, cause the dental material to set up and cure rather quickly. These photoinitiators are particularly sensitive to visible light in the vicinity of about 470 nm.

The light rod 16 of this embodiment is formed of a fused fiberoptic bundle, but in other embodiments could employ a liquid light guide. In either event, the light rod is especially effective in carrying the blueviolet visible light generated by the lamp 34 and which is required for curing the material 50.

Figure 3:
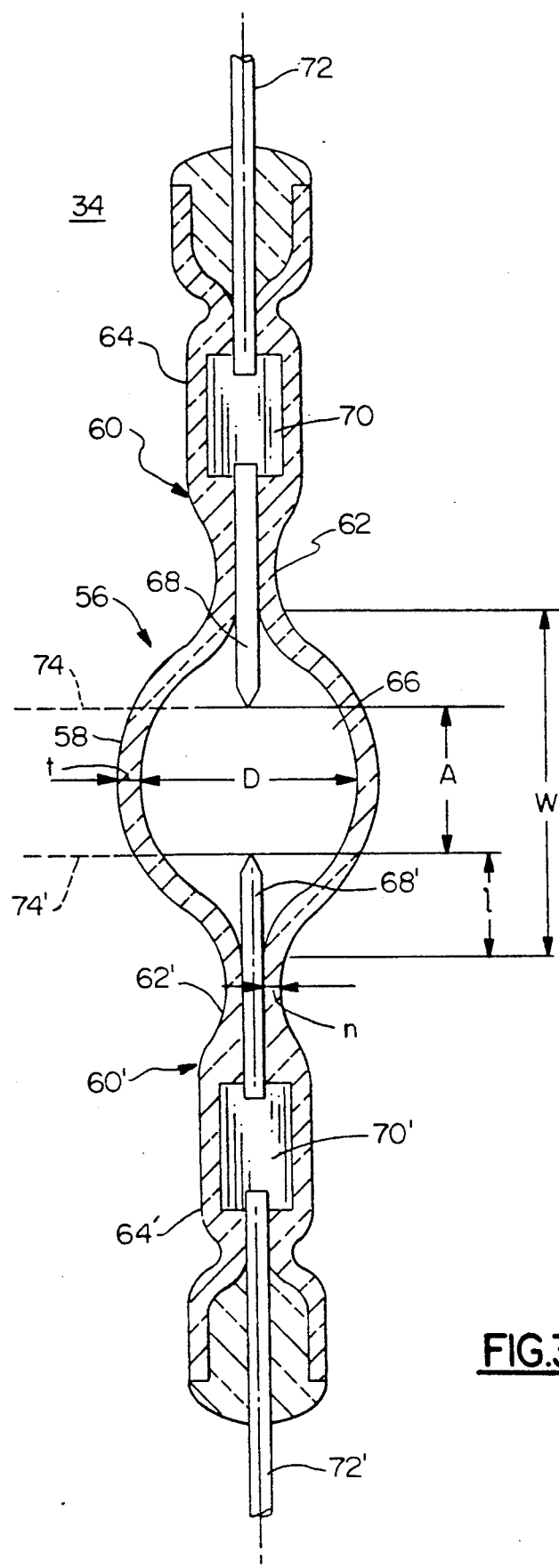
FIG. 3 shows a low watt metal halide lamp according to an embodiment of the present invention which serves as the light source for the dental light gun device of FIG. 1.

The high efficiency, low watt metal halide discharge lamp 34 is shown in greater detail in FIG. 3. Lamp 34 has an input power of 20 watts. Lamp 34 is of double-ended design and comprises a generally spherical fused quartz envelope 56 having a bulb portion 58 and a pair end shanks 60, 60'. End shanks 60, 60' include respective transitional neck portions 62, 62' and respective stem portions 64, 64'. Defined by the walls of bulb portion 58 is an arc chamber 66.

Contained within arc chamber 66 is a fill of mercury, argon gas and the metal halide, indium iodide or indium triiodide. The mercury and the metal halide are condensed on the interior surface of the walls of bulb portion 58 at room temperature. A pair of straight shanked tungsten wire electrodes 68, 68' extend into arc chamber 66 from neck portions 62, 62' respectively. Electrodes 68, 68' are generally of equal length and each have a pointed tip. Lamp 34 is D.C. operated. However, the aspects of the present invention are equally applicable to A.C. operated metal halide lamps. Electrode 68' is the cathode and has a diameter of about 0.2032 mm. Electrode 68 is the anode and has a diameter of about 0.254 mm. Cathode 68' is made of thoriated tungsten wire.

The tips of electrodes 68, 68' are spaced apart from one another by a distance A. The distance is sometimes referred to as the arc gap. Electrodes 68, 68' are lap welded to respective molybdenum ribbon foils 70, 70'. Lamp envelope 56 is hermetically sealed at ribbon foils 70, 70'. A pair of molybdenum wire inleads 72, 72' are lap welded respectively to ribbon foils 70, 70'. An assembly, including a ribbon foil and a wire inlead is referred to herein as an inlead assembly. Inleads 72, 72' are electrically connected to respective pin conductors provided in lamp assembly 32, as shown in FIG. 2.

Critical dimension points of lamp 34 are defined in FIG. 3. Transitional neck portions 62, 62' each have a minimum wall thickness designated as n. The wall thickness n should not exceed about 1.5 mm in order to achieve high efficiency lamp operation at power inputs of 35 watts and below. By maintaining the wall thickness n not greater than 1.5 mm, thermal losses through neck portions 62, 62' are minimized resulting in hotter end regions in the arc chamber of lamp 34, which in turn results in greater operating efficiencies. In the preferred embodiment, the neck portion wall thickness n is about 0.75 mm.

With further reference to FIG. 3, it is shown that bulb portion 58 of envelope 56 has a wall thickness t. Wall thickness t is defined as the maximum wall thickness established along a centrally disposed segment of bulb portion 58, bounded by two imaginary parallel planes 74, 74' that are located at the tips of the electrodes of lamp 34, as shown in FIG. 3. Wall thickness t of lamp 34 should not exceed about 0.5 mm in order to minimize thermal losses through the wall of bulb portion 58 and to ensure greater operating efficiency at low power inputs. In the preferred embodiment, thickness t of lamp 34 is about 0.26 mm. Wall thickness t is substantially uniform over the centrally disposed segment of bulb portion 58, resulting in a more even thermal distribution within arc chamber 66 during lamp operation.

The proportions of the arc chamber can be expressed in terms of its internal length W and internal diameter D. As shown in FIG. 3, the internal arc chamber length W is defined between the points where the electrodes emerge from the fused quartz envelope inside the arc chamber. The internal diameter D of the arc chamber is the diameter at the maximum transverse cross-section of the arc chamber. In most cases, this point is at or near the center of the arc chamber. In the preferred embodiment, lamp 34 will have an arc chamber internal diameter D within a range from about 0.34 to about 0.37 cm, and an internal arc chamber length W within a range from about 0.65 to about 0.76 cm.

A useful expression in considering arc chamber geometry is the aspect ratio. The aspect ratio of the arc chamber is defined by the ratio of arc chamber length W divided by internal diameter D, (W/D). In the preferred embodiment, lamp 34 will have an aspect ratio in the range from about 1.8 to about 2.2.

As shown in FIG. 3, the insertion depth $l$ of the electrodes of lamp 34 is defined as the distance over which the electrodes project into the arc chamber from the point where the electrode emerge from the fused quartz envelope. In the preferred embodiment, the insertion depth of electrodes 68, 68' of lamp 34 is greater than 2.0 mm, and in many cases will be within the range of about 2.1 to about 2.7 mm.

With further reference to FIG. 3, there is shown the arc gap or distance dimension A. Arc distance is a measure of the length of the arc produced between the electrodes of the lamp. This dimension is usually taken as the distance between the tips of the electrodes. In the preferred embodiment, the arc distance A of lamp 34 will be in the range from about 2.0 to about 2.5 mm.

The arc distance A is used in determining the arc loading, an important design parameter affecting lamp efficiency. Arc loading is defined as the input power to the lamp divided by the arc distance A. For a given power input, a short arc distance results in a high arc loading. High arc loadings generally result in higher efficiencies for the low watt metal halide lamps of the present invention. In the preferred embodiment, the arc loading of lamp 34 will be in the range from about 72 to about 111 w/cm, resulting in adequate spectral efficiency levels for most photo-curing applications.

Another design parameter for lamp 34 is wall loading. Wall loading is defined as the input power in watts to the lamp divided by the external radiating surface area of the arc chamber. As an approximation, the radiating surface area is taken as the external surface of the lamp envelope, excluding the end shanks. Excessive wall loading can cause envelope devitrification at an accelerated rate, resulting in poor lumen maintenance and shortened lamp life. The wall loading of lamp 34 should be maintained below 35 watts/cm$^2$ to ensure adequate lumen maintenance and lamp life for the intended photo-curing applications. In the preferred embodiments, the wall loading of lamp 34 is approximately 10 watts/cm$^2$.

Yet another design parameter for lamp 34 is the insertion factor Y. Insertion factor Y corresponds to the formula:

$$Y = (W - A) / W.$$

For photo-curing applications, the electrode insertion depth 1 at both ends of the arc chamber will be approximately equal. Therefore, Y follows the relationship:

$$Y = 2(1) / W.$$

In the preferred embodiment of the present invention, the insertion factor is greater than a value of 0.6.

The mercury loading contained within arc chamber 66 of lamp 34 is approximately 1.4 mg. The metal halide additive contained in arc chamber 66 is indium iodide, and the indium iodide loading in arc chamber 66 will be in the range of from about 0.075 to about 0.225 mg. The inert gas contained in arc chamber 66 is argon at an ambient pressure of about 500 torr. The internal volume of arc chamber 66 is approximately 0.04 cm$^3$. The voltage drop across the arc gap A of lamp 34 is approximately 55 volts. Any known starting and operating circuit could be employed with lamp 34.

The emission spectrum for the lamp 34 is shown in pertinent part in FIG. 4. Most of the light produced by this lamp falls in the wavelength range between 400 nm and 500 nm, as shown in the InI spectral discharge curve 80. In this case, the halide additive InI salt has a spectral line 82 at about 455 nm, and the mercury vapor has a small peak at its spectral discharge line at about 436 nm. The peak sensitivity wavelength 84 for photo-curable dental restoration material, i.e. 470 nm, occurs in this 400-500 nm band but above the indium iodide principal spectral line 82. However, because of the operating conditions of lamp 34, the InI operating pressure is increased sufficiently to broaden the emission as shown, so that the emission peak spans the wavelengths of 430 to 490 nm. There is an inversion 86 at the position of the indium iodide spectral line. This occurs because of reabsorption of photons at 455 nm by the indium iodide molecules in the arc plasma. This energy is reradiated at other wavelengths separated somewhat from 455 nm, producing both the spectral line reversal or inversion 86, and the broadening of the InI discharge peak. The mercury and additive vapor pressures should be as high as achievable for the quartz envelope to obtain optimal efficiency within this wavelength band. The intensity of discharge at 470 nm can be compared with the light emitted from a conventional tungsten halogen lamp of the type often used in other dental irradiation units. Here, a spectral curve 88 represents the output of a 35-watt tungsten halogen lamp. There, the output at 470 nm is only two milliwatts per square centimeter as compared with seven milliwatts per square centimeter for the 20-watt lamp of this invention. With the present invention, heat management is less of a problem because of the relatively low power consumption, i.e., 20 watts. Continuous operation is possible.

The warm up time for this lamp 34 is on the order of ten seconds, and the curing time with the dental irradiation unit 10 is from 30 seconds to about 90 seconds for composite filing material, and only a few seconds for dental impression material.

The envelopes of the lamps according to the present invention may be manufactured on a glass blowing lathe having a headstock and a tailstock, capable of both moving synchronously. The process begins with a piece of fused quartz tubing having an outside diameter of approximately 3 mm and an inside diameter of approximately 2 mm. Once the tubing is loaded into the lathe, a point along the tubing is heated with a burner until the quartz is plastic. Then, both the tailstock and the headstock of the lathe are moved synchronously apart at equal rates, to cause the tubing to be pulled with equal force at both ends and stretched to a desired length. The stretched portion of tubing is then heated slightly to shrink its diameter to a desired point.

This sequence of steps is repeated at a second point displaced from the initial point by a distance approximating the desired arc chamber length. The next step is to heat the section of tubing between the stretched points until the quartz is plastic. At the same time, nitrogen under pressure is introduced into the tubing to cause the plastic section of tubing to blow out to a desired arc chamber shape. The completed envelope is then detached from the tubing remaining in the lathe.

Once the envelope has been formed, the lamp is assembled. During the assembly process, the quartz envelope is held in a vertical position. An electrode assembly, including a molybdenum inlead wire, a molybdenum ribbon foil, and a tungsten electrode, is lowered into the top envelope shank. At the same time, the interior of the envelope is continuously flushed with a suitable inert dry gas, such as argon, which is directed upwardly through the envelope. Once the electrode part of the assembly is positioned correctly into the arc chamber, the neck of the top envelope shank is heated with two burners, one on each side of the neck. The heating is just sufficient to slightly shrink the neck tightly around the electrode shank. Wetting of the quartz does not occur around the electrodes and, therefore, a hermetic seal is not formed. The flushing of dry gas into the envelope continues to ensure that contamination is minimized.

Once the neck portion of the envelope shank is secured around the electrode shank, the burners are displaced upward to heat the stem portion of the envelope shank. The heating at this point causes shrinking and wetting of the quartz around the ribbon foil to establish a hermetic seal. Beyond this point, the stem is heated to cause it to shrink securely around the inlead wire. During any steps involving heating of the shank, the bulb portion of the envelope is continuously cooled by water. Care is always taken throughout the process to avoid contamination inside the envelope.

The position of the partially assembled lamp is rotated 180° so that the top envelope shank is now at the bottom. Inert dry gas continues to be flushed through the open shank into the envelope. At the same time, an indium iodide pill is transferred into the bulb portion through the open shank. The specified amount of mercury is also transferred into the bulb portion through the open shank. Finally, an electrode assembly is lowered into the open envelope shank and sealed therein as earlier described to complete the assembly process. Before sealing, an amount of inert gas at a specified pressure is introduced into the bulb portion of the envelope.

While this invention has been described in detail with respect to one preferred embodiment, it should be understood that the invention is not limited to that precise embodiment. Rather, many modifications and variations would present themselves to those skilled in the art without departing from the scope and spirit of this invention, as defined in the appended claims.

What is claimed is:

1. A low-watt metal halide discharge lamp for use in photo-curing photo-curable compositions, comprising:
   an envelope made of light transmissive material, having walls that define an arc chamber volume;
   a fill of mercury, inert gas and a metal halide additive that includes an indium halide contained within said arc chamber volume, said mercury and said metal halide additive being adapted to vaporize during operation of said lamp and produce radiation energy that is maximized within the wavelength range between 400 and 500 nm;
   a pair of electrodes, extending into said arc chamber volume, having electrode tips spaced apart from one another by a predetermined distance within said arc chamber volume; and
   a pair of inlead assemblies electrically coupled to said pair of electrodes respectively and passing from said electrodes through a sealed section in said envelope to the exterior of said lamp;
   wherein said lamp has a power input rating of not more than 35 watts, and said lamp contains amounts of indium halide and of mercury sufficient to cause an operating vapor pressure high enough to result in a spectral line reversal at the principal spectral line of said indium halide, and a broadband radiation in said range of 400–500 nm.

2. The lamp as recited in claim 1, wherein said indium halide is indium iodide.

3. The lamp as recited in claim 1, wherein said indium halide is indium triiodide.

4. The lamp as recited in claim 1, wherein said lamp has a power input reading in the range of from about 18 to 22 watts.

5. The lamp as recited in claim 1, wherein said lamp has a power input reading of about 20 watts.

6. The lamp as recited in claim 2, wherein said lamp has a power input of not more than 35 watts; and wherein said envelope includes a bulb portion, a pair of transitional neck portions extending from said bulb portion and a pair of stem portions extending from said transitional neck portions respectively, said bulb portion of said envelope having walls that define said arc chamber volume and have an external surface area of such value as to produce a wall loading not exceeding about 35 watts/cm$^2$.

7. The lamp as recited in claim 6, wherein said pair of electrodes extend into said arc chamber volume from said pair of said neck portions respectively, said neck portions of said envelope each having a wall surrounding a segment of said electrodes respectively, the walls of said neck portions each having a stretched section with a minimum wall thickness not exceeding about 1.5 mm.

8. The lamp as recited in claim 7, wherein said lamp has a power input of about 20 watts.

9. The lamp as recited in claim 8, wherein said walls, that define said arc chamber volume, have a substantially uniform thickness over a centrally disposed segment defined between two imaginary parallel planes located at the electrode tips respectively; said walls having a thickness not exceeding about 0.5 mm over said centrally disposed segment.

10. The lamp as recited in claim 9, wherein said arc chamber volume has an aspect ratio in the range from about 1.8 to about 2.2.

11. The lamp as recited in claim 10, wherein the insertion depth l of said electrodes is greater than 2.0 mm.

12. The lamp as recited in claim 11, wherein said fill includes loading of about 1.4 mg.

13. The lamp as recited in claim 12, wherein said fill includes an indium iodide loading in the range from about 0.075 to about 0.225 mg.

14. The lamp as recited in claim 2, wherein said fill includes a mercury loading of about 1.4 mg and an indium iodide loading in the range from about 0.075 to about 0.225 mg.

15. The lamp as recited in claim 1, wherein said mercury fill is about 35 mg per cm$^3$ of said arc chamber volume, and said indium halide fill is at least about 1.9 mg per cm$^3$.

16. The lamp as recited in claim 1, wherein said fills of mercury and of iodide of indium are sufficiently high to cause a high vapor operating pressure that is characterized by a broadband radiation of at least 40 nm on either side of the said principal spectral line, and by said spectral line reversal at said principal spectral line.

* * * * *